United States Patent [19]

Chang et al.

[11] 4,044,061
[45] Aug. 23, 1977

[54] PREHEATING METHANOL EFFECTS STEADY STATE OPERATION OF CONVERSION TO GASOLINE

[75] Inventors: Clarence D. Chang, Princeton, N.J.; Anthony J. Silvestri, Morrisville, Pa.; John C. Zahner, Princeton, N.J.

[73] Assignee: Mobil Oil Corporation, New York, N.Y.

[21] Appl. No.: 658,633

[22] Filed: Feb. 17, 1976

Related U.S. Application Data

[63] Continuation-in-part of Ser. No. 508,390, Sept. 23, 1974, abandoned.

[51] Int. Cl.² .............................................. C07C 1/22
[52] U.S. Cl. ........................ 260/668 R; 260/668 A; 260/671 C; 260/672 T; 260/676 R; 260/677 R; 260/682; 208/118; 208/120; 208/135; 208/141
[58] Field of Search ................... 260/668 R, 682, 676, 260/671, 677, 672 T, 668 A; 208/135, 141, 118, 120

[56] References Cited

U.S. PATENT DOCUMENTS

| | | | |
|---|---|---|---|
| 2,051,774 | 8/1936 | Kleinschmidt | 252/373 |
| 2,884,370 | 4/1959 | Nonenmacher et al. | 208/97 |
| 3,666,423 | 5/1972 | Muenger | 252/373 |
| 3,894,107 | 7/1975 | Butter et al. | 260/668 R |

Primary Examiner—Veronica O'Keefe
Attorney, Agent, or Firm—Charles A. Huggett; Carl D. Farnsworth

[57] ABSTRACT

The conversion of methanol to gasoline boiling hydrocarbons in a thermally balanced operation with a special group of zeolite catalysts having a constraint index of 1 to 12, a silica to alumina ratio of at least about 12 and a crystal density of not substantially lower than about 1.6 grams per cubic centimeter is described. The steady state operation of the process is improved by feeding methanol preheated to a selected temperature proximate to its boiling point so that the heat required thereafter to vaporize the feed and to raise its temperature to conversion temperature is substantially equal to the exothermicity of the conversion itself.

10 Claims, 2 Drawing Figures

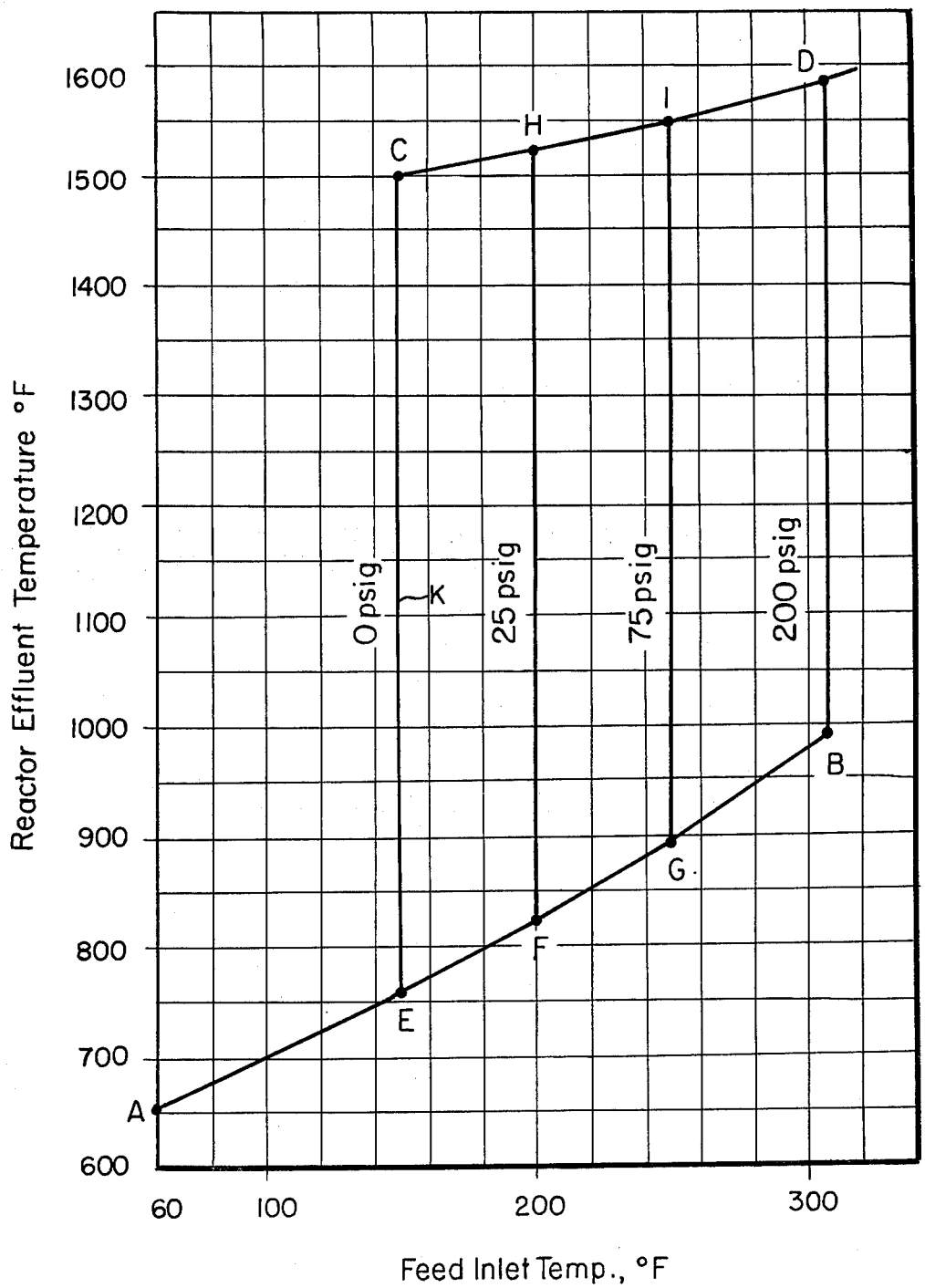

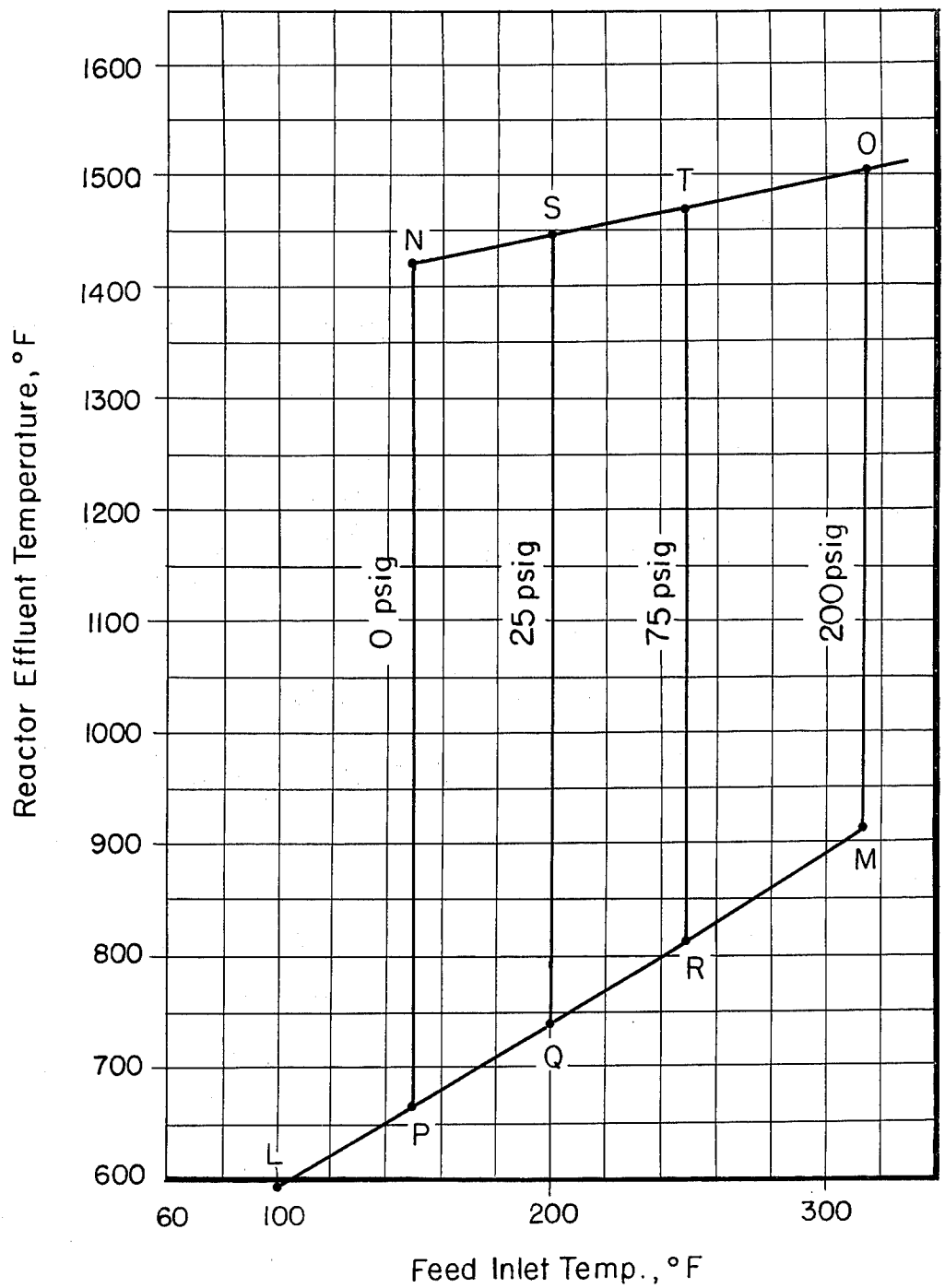
FIGURE II
ΔH = 689 BTU/LB
Pressure = 0-200 psig

PREHEATING METHANOL EFFECTS STEADY STATE OPERATION OF CONVERSION TO GASOLINE

This application is a continuation-in-part of application Ser. No. 508,390, filed Sept. 23, 1974 now abandoned.

The special zeolite catalysts referred to herein utilize members of a special class of zeolites exhibiting some unusual properties. These zeolites induce profound transformations of aliphatic hydrocarbons to aromatic hydrocarbons in commercially desirable yields and are generally highly effective in alkylation, isomerization, disproportionation and other reactions involving aromatic hydrocarbons. Although they have unusually low alumina contents, i.e. high silica to alumina ratios, they are very active even with silica to alumina ratios exceeding 30. This activity is surprising since catalytic activity of zeolites is generally attributed to framework aluminum atoms and cations associated with these aluminum atoms. These zeolites retain their crystallinity for long periods in spite of the presence of steam even at high temperatures which induce irreversible collapse of the crystal framework of other zeolites, e.g. of the X and A type. Furthermore, carbonaceous deposits, when formed, may be removed by burning at higher than usual temperatures to restore activity. In many environments, the zeolites of this class exhibit very low coke forming capability, conductive to very long times on stream between burning regenerations.

An important characteristic of the crystal structure of this class of zeolites is that it provides constrained access to, and egress from, the intra-cyrstalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful as catalysts in this invention possess, in combinatin: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The zeolites useful as catalysts in this invention freely sorb normal hexane and have a pore dimension greater than about 5 Angstroms. In addition, their structure must provide constrained access to some larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is substantially excluded and the zeolite is not of the desired type. Zeolites with windows of 10-membered rings are preferred, although excessive puckering or pore blockage may render these zeolites substantially ineffective. Zeolites with windows of twelve-membered rings do not generally appear to offer sufficient constraint to produce the advantageous conversions desired in the instant invention, although structures can be conceived, due to pore blockage or other cause, that may be operative.

Rather than attempt to judge from crystal structure whether or not a zeolite possesses the necessary contrained access, a simple determination of the "constraint index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F for at least 15 minutes. The zeolite is then flushed with helium and the temperature adjusted between 550° F and 950° F to give an overall conversion between 10% and 60%. The mixture of hydrocarbons is passed at 1 liquid hourly space velocity (i.e., 1 volume of liquid hydrocarbon per volume of catalyst per hour) over the zeolite with a helium dilution to give a helium to total hyrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} \text{(fraction of n-hexane remaining)}}{\log_{10} \text{(fraction of 3-methylpentane remaining)}}$$

The constraint index approximates the ratio of the cracking rate constants for the two hydrocarbons. Catalysts suitable for the present invention are those which employ a zeolite having a constraint index from 1.0 to 12.0. Constraint Index (CI) values for some typical zeolites including some not within the scope of this invention are:

| CAS | C.I. |
| --- | --- |
| ZSM-5 | 8.3 |
| ZSM-11 | 8.7 |
| ZSM-35 | 4.5 |
| TMA Offretite | 3.7 |
| ZSM-12 | 2 |
| ZSM-38 | 2 |
| Beta | 0.6 |
| ZSM-4 | 0.5 |
| Acid Mordenite | 0.5 |
| REY | 0.4 |
| Amorphous Silica-alumina | 0.6 |
| Erionite | 38 |

The above-described Constraint Index is an important jand even critical, definition of those zeolites which are useful to catalyze the instant process. The very nature of this parameter and the recited technique by which it is determined, however, admit of the possibility that a given zeolite can be tested under somewhat different conditions and thereby have different constraint indexes. Constraint Index seems to vary somewhat with severity of operation (conversion). Therefore, it will be appreciated that it may be possible to so select test conditions to establish multiple constraint indexes for a particular given zeolite which may be both inside and outside the above defined range of 1 to 12.

Thus, it should be understood that the "Constraint Index" value as used herein is an inclusive rather than an exclusive value. That is, a zeolite when tested by any combination of conditions within the testing definition set forth herein above to have a constraint index of 1 to 12 is intended to be included in the instant catalyst definition regardless that the same identical zeolite tested under other defined conditions may give a constraint index value outside of 1 to 12.

The class of zeolites defined herein is exemplified by ZSM-5, ZSM-11, ZSM-12, ZSM-21, ZSM-35, ZSM-38 and other similar material. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

U.S. application Ser. No. 528,061 filed Nov. 29, 1974, the entire contents of which are incorporated herein by reference, describes a zeolite composition including a method of making it. This composition is designated ZSM-35 and is useful in this invention.

U.S. application Ser. No. 528,060, filed Nov. 29, 1974, now abandoned, describes a zeolite composition including a method of making it. This composition is designated ZSM-38 and is useful in this invention.

The x-ray diffraction pattern of ZSM-21 appears to be generic to that of ZSM-35 and ZSM-38. Either or all of these zeolites is considered to be within the scope of this invention.

The specific zeolites described, when prepared in the presence of organic cations, are substantially catalytically inactive, possibly because the intracrystalline free space is occupied by organic cations from the forming solution. They may be activated by heating in an inert atmosphere at 1000° F for one hour, for example, followed by base exchange with ammonium salts followed by calcination at 1000° F in air. The presence of organic cations in the forming solution may not be absolutely essential to the formation of this special type zeolite; however, the presence of these cations does appear to favor the formation of this special type of zeolite. More generally it is desirable to activate this type zeolite by base exchange with ammonium salts followed by calcination in air at about 1000° f for from about 15 minutes to about 24 hours.

Natural zeolites may sometimes be converted to this type zeolite by various activation procedures and other treatments such as base exchange, steaming, alumina extraction and calcination, alone or in combinations. Natural minerals which may be so treated included ferrierite, brewsterite, stilbite, dachiardite, epistilbite, heulandite and clinoptilolite. The preferred crystalline aluminosilicates are ZSM-5, ZSM-11, ZSM-12 and ZSM-21, with ZSM-5 particularly preferred.

The zeolites used as catalysts in this invention may be in the hydrogen form or they may be base exchanged or impregnated to contain ammonium or a metal cation complement. It is desirable to calcine the zeolite after base exchange. The metal cations that may be present include any of the cations of the metals of Group I through VIII of the periodic table. However, in the case of Group IA metals, the cation content should in no case be so large as to substantially eliminate the activity of the zeolite for the catalysts being employed in the instant invention. For example, a completely sodium exchanged H-ZSM-5 appears to be largely inactive for shape selective conversions required in the present invention.

In a preferred aspect of this invention, the zeolites useful as catalysts herein are selected as those having a crystal framework density, in the dry hydrogen form, of not substantially below about 1.6 grams per cubic centimeter. It has been found that zeolites which satisfy all three of these criteria are most desired. Therefore, the preferred catalysts of this invention are those comprising zeolites having a constraint index as defined above of about 1 to 12, a silica to alumina rate of at least about 12 and a dried crystal density of not substantially less than about 1.6 grams per cubic centimeter. The dry density for known structures may be calculated from the numer of silicon plus aluminum atoms per 1000 cubic Angstroms, as given, e.g., on page 19 of the article on Zeolite Structure by W. M. Meier. This paper, the entire contents of which are incorporated herein by reference, is included in "Proceedings of the Conference on Molecular Sieves, London, April, 1967" published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively small amount of free space within the crystal, which might be expected to result in more stable structures. This free space, however, seems to be important as the locus of catalytic activity.

Crystal framework densities of some typical zeolites including some which are not within the purview of this invention are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

A matrix binder can be employed with the special zeolite conversion catalyst. The zeolite catalyst can be incorporated, combined, dispersed, or otherwise intimately admixed with the matrix in such proportions that a resulting product will contain from b 1% to 95% by weight and preferably from 10% to 70% by weight of the zeolite in the final catalyst composite.

The term "matrix" includes inorganic composition of which the zeolites can be incorporated, combined, dispersed, or otherwise intimately admixed wherein the matrix may be catalytically active or inactive, porous or non-porous. It is to be understood that the porosity of the composition employed as a matrix can be either inherent in the particular material or it can be introduced by mechanical or chemical means. Representative of matrices which can be employed include metals and alloys thereof, sintered metals, and sintered glass, asbestos, silicon carbide, aggregates, pumice, firebrick, diatomaceous earths, alumina and inorganic oxides. Inorganic compositions, especially those comprising alumina and those of a siliceous nature are preferred. Of these matrices, inorganic oxides such as clay, chemically-treated clays, silica, silica alumina, etc., as well as alumina, are particularly preferred because of their superior porosity, attrition resistance and stability. Techniques for incorporating a zeolite catalyst into a matrix are known in the art and set forth in U.S. Pat. No. 3,140,253.

This invention relates to the conversion of lower alcohols such as methanol to higher boiling hydrocarbons. It more particularly refers to a method of operation directed to improvements in heat balancing the conversion of lower alcohols such as methanol.

Application Ser. No. 387,222, filed Aug. 9, 1973, now U.S. Pat. No. 3,894,106 discloses the conversion of lower alcohols and analogs thereof to higher hydrocarbons particularly highly aromatic gasoline boiling range hydrocarbons. The conversion is disclosed to be carried out at elevated temperatures in contact with a special group of catalyst defined therein to be crystalline alumino-silicate zeolites having a constraint index of 1 to 12, a silica to alumina ratio of at least 12 and, preferably, a crystal density of not substantialy below about 1.6 grams per cubic centimeter. Representative catalyst species disclosed were ZSM-5, ZSM-11, ZSM-12, and ZSM-21.

The conversion of heteroatom containing lower organic compounds such as the lower alcohols to higher boiling hydrocarbons is in some cases quite exothermic. The restructuring of methanol to higher boiling hydrocarbons is most interesting and highly exothermic, and therfore problemsome.

It has been discovered that there is a unique relationship between the amount of heat generated in the exothermic conversion of methanol to gasoline boiling hydrocarbons and the amount of heat required to vaporize methanol and then raise the temperature of the vapor to a desired conversion temperature. The essence of this invention is therefore concerned with taking advantage of this unique phenomenon during steady-state operation of the process and after start-up, and to heat balance the process by feeding methanol selectively preheated to a desired level as a function of operating pressure before contacting the catalyst in a conversion zone. Although it is possible to feed the preheated methanol to the conversion zone at various temperatures above and below its vapor temperature, depending on operating pressure and exothermic heat release in the operation, the essence of this invention is directed to preheating the methanol feed to a selected temperature permitting maintaining the reaction adiabatic temperature below 900° F so that exothermic generated heat will be controlled by balancing the said heat of reaction against the latent and sensible heats of the methanol feed.

It will be apparent from the following that this invention is generally suitable for use in steady-state exothermic conversion processes. When converting methanol to gasoline boiling hydrocarbons, conversion temperatures are at least about 600° F and may be as high as about 950° F but more usually are less than 900° F. Therefore, external heat input is required during the initial, transient start-up period. Therefore, a preferred start-up procedure is to preheat the feed methanol to an elevated temperature sufficient to vaporize a portion if not all the feed and initiate conversion at a temperature of at least about 700° F. The conversion operation is sufficiently rapid so that vaporization of feed methanol can be discontinued or reduced as the operation demands as soon as a desired high temperature hydrocarbon product is formed sufficient to practice the concepts of this invention.

The exothermic heat of reaction ($\Delta H$) or heat release of the operation can vary somewhat depending upon the product distribution desired. By a judicious selection of operating conditions, i.e., temperature, pressure, catalyst activity, and space velocity, one can effectively select a product distribution and hence the heat release of the exothermic reaction herein contemplated. However, the exothermic heat of reaction of the operation is ordinarily of the order of 400 calories per gram of total product comprising hydrocarbon and water. An exothermic heat release ($\Delta H$) operation in the range of 689 to 747 BTU/LB of total product corresponding respectively to 383 and 415 cal/gm is more fully discussed below.

The conversion of methanol to gasoline boiling range hydrocarbons, in addition to being exothermic, involves the production of water. The reaction mechanism for the conversion includes dehydration of methanol to form one mole of water for each carbon atom of the hydrocarbon product. Thus, in the conversion of methanol to higher hydrocarbons, one mole of water is produced for each mole of methanol converted to hydrocarbon.

The zeolite catalyst employed in the operation is unique with respect to its ability to catalyze the conversion of methanol to gasoline boiling hydrocarbons. However, in common with other types of aluminosilicate catalysts, although to a much lesser extent, water at higher temperatures may reduce its activity. Thus, to a minor extent, water produced during the methanol conversion reaction may gradually reduce the activity of the zeolite catalyst. This reduction in activity, for the purposes of this application, will be called "steam aging".

The rate at which the steam aging occurs is believed to increase with the temperature of the conversion reaction. The exothermic heat of the methanol conversion reaction is of the order of about 689 to 747 BTU/LB of total product. Specifically at 720 BTU/LB (400 calories per gram) of hydrocarbons, and water produced, an adiabatic temperature rise of 1232° F has been calculated to be possible in this reaction. Thus, under adiabatic conditions, the temperature of the reaction products obtained by contacting methanol with the zeolite catalyst at an initial temperature of 700° F can be as high as 1932° F. Accordingly, temperature control of the conversion reaction is absolutely imperative.

By the method and process combination of the invention, a commercially realistic and effective temperature control mechanism is provided for the conversion of methanol to gasoline boiling hydrocarbons. This conversion temperature control mechanism is effected at least in part by employing the feed methanol in a preheated condition which is partially vapor under low pressure operations but in all liquid phase condition when employing a pressure of 75 psig and higher as a primary temperature controlling agent. The preheated feed methanol as a function of operating pressure is brought in contact with a special crystalline zeolite conversion catalyst herein identified at a feed temperature which permits the absorption of reaction heat within the catalyst conversion zone environment sufficient to vaporize the feed to reaction temperature and convert the thus vaporized methanol to gasoline hydocarbons and water.

The conversion zone utilized in the instant process may be a fixed, fluidized or fluid transport type catalyst bed arrangement. Appropriate heat exchange apparatus may be provided within and outside the catalyst bed as desired or required by the particular reactor design chosen to preheat the feed within the limits herein defined.

The process combination of the invention may be accomplished with a catalyst system containing a single catalyst bed or a plurality of sequentially arranged catalyst beds. It is to be understood that the process of the invention may be carried out in a catalyst system employing one or more fixed beds of the catalyst, a fluid catalyst system or a combination thereof. Each bed of catalyst may be contained in a single or separate reactor and the reactors sequentially connected by suitable piping means or other form of passageway for passage of methanol and a reaction product mixture thereof downstream from one catalyst bed to the other. On the other hand, where a plurality of catalyst beds are employed, they all may be contained in a single reactor of the same or increasing bed thickness in the direction of flow to assist with controlling exothermic reaction heat.

With respect to the conduct of the desired methanol conversion reaction, the temperature thereof is at least 600° F. Temperatures up to about 900° F may also be employed, but preferably the adiabatic reactor effluent temperatures are maintained below about 850° F for the production of gasoline boiling materials. The pressure may be from about atmospheric up to several hundred pounds pressure but preferably below about 500 psig. The weight per hour space velocity (WHSV) of the methanol charged is within the range of 0.5 to 1000. It will be understood, of course, that in an embodiment of this invention involving multiple injection of methanol feed in the direction of reactant flow each introduction of liquid methanol into the reaction products in the catalyst system will effect a temperature control and increase the space velocity thereof downstream from the point of entry.

The reaction mixture recovered from the catalyst system will contain aliphatic and aromatic gasoline boiling range hydrocarbons, lighter aliphatic hydrocarbons and water. It may also contain some unreacted methanol or oxygenated intermediates and hydrocarbons boiling above the gasoline boiling range. Product recovery may be by a seris of unit operations with a relatively simple condensation and decantation to separate a gaseous phase, a liquid hydrocarbon phase and an aqueous phase from each other. This condensation arrangement is suitably accomplished in heat exchange relation with cold methanol feed to heat the cold feet to a predetermined and desired elevated temperature prior to entry into the conversion zone.

It is readily apparent from the discussion herein presented that applicants' invention is particularly concerned with the technology of exothermic reactions in a very particular aspect. That is, the invention is concerned with the finding that the heat of reaction is such that it equals the latent heat of vaporization plus the sensible heat required to take for example a methanol charge up to reaction temperature. Therefore, preheating the methanol charge to a desired temperature below its boiling point or just at incipient vaporization depending on pressure employed after which a desired heat gain in the conversion of the methanol is maintained is a unique combination of processing variables. Applicants' invention is not limited to effecting a heat exchange between hot reaction product and cold reactant feed since only a very small portion of the available heat is utilized for that purpose. On the other hand, as shown by the following specific discussion, applicants' invention is concerned with operating within relatively specific processing envelope variables involving highly exothermic reactions to achieve desired result in the conversion of methanol to gasoline boiling material.

DISCUSSION OF SPECIFIC EMBODIMENTS

Referring now to FIGS. I and II, different processing envelopes are shown graphically for operating pressures within the range of 0 to 200 psig. FIG. I identifies the processing envelope of an adiabatic operation comprising a ΔH (heat gain) of 747 BTU/LB producing an aromatic gasoline product. FIG. II identifies the processing envelope of an adiabatic operation comprising a ΔH (heat gain) of 689 BTU/LB. FIG. I identifies processing envelopes for pressures of 0, 25, 75 and 200 psig at adiabatic operating conditions comprising a heat release (ΔH) of 747 BTU/LB of product. Thus in the graphical envelopes of FIG. I, line AB represents the 100 percent liquid feed line and line CD represents the 100 percent vapor feed line. In this combination of operating envelopes, line AEC is the 0 psig pressure envelope, AFH is the 25 psig operating envelope, AGI is the 75 psig operating envelope and ABD is the 200 psig operating pressure envelope. This figure demonstrates the need to restrict preheating of the feed to maintain the reactor effluent temperature below 900° F as a function of the operating pressure.

Referring now to FIG. I, the solid line AB of the graphical envelopes representing the 100 percent liquid phase of the feed provides a relationship of liquid feed preheat and adiabatic reactor effluent temperature when processing under exothermic temperature conditions providing a ΔH (heat gain) of about 747 BTU/LB of product comprising aromatic gasoline. On the other hand, line CD of the envelopes show the relationship between reactor effluent temperature when preheating the feed to 100 percent vapor condition for the different pressure operations identified. In addition, the vertical lines EC, FH, GI, and BD for the different pressure operations identified can be proportioned to identify substantially any partially vaporized feed and the adiabatic reactor effluent temperature one would obtain under such an operating condition. For example, if point K of line EC represent a 50% vapor feed in a 0 psig pressure operation then one could expect to obtain a reactor effluent temperature of about 1125° F. This, of course, will vary with pressure as shown by the processing envelope. For the above to be true, it must be recognized that vertical line EC or any of the other vertical lines identified represent the heat absorbed by the liquid feed to obtain any given percent of vaporization. Thus, the ore heat that is absorbed by the liquid will also operate to increase the degree of vaporization thereof.

The operating envelopes of FIG. I are more meaningful when it is remembered that it is particularly desired in the conversion of methanol to maintain the adiabatic reactor effluent temperature below 900° F and more usually below about 800° F but above about 650° F. For example, in the operating envelopes of the 75 and 200 psig operation, preheating of the feed must not exceed about 250° F in order to maintain a reactor effluent temperature not in excess of about 900° F for the ΔH operation of 747 BTU/LB. On the other hand, the 0 and 25 psig pressure operations may be operated with a partially vaporized feed without exceeding desired reactor effluent temperatures below about 900° F. It will be noted that for the 25 psig operation it is essential to maintain the feed at least 25° below its boiling point in order to maintain a reactor effluent temperature of 800° F or less.

It is readily apparent from a study of the operating modes of FIG. I that when operating at pressure of 25 psig or higher it is highly desirable to retain the preheated feed in an all liquid condition in order to avoid exceeding desired reactor effluent adiabatic temperature less than 900° F.

FIG. II like FIG. I identifies processing envelopes for pressures of 0, 25, 75 and 200 psig and adiabatic operations comprising heat release (ΔH) of 689 BTU/LB of product and comprising an olefinic gasoline product. Thus, in the graphical envelopes of FIG. II line LM represents the 100 percent liquid feed line and line NO represents the 100 percent vapor feed line. Furthermore, in the combination of operating envelopes represented by FIG. II, line LPN is the 0 psig pressure envelope, LQS in the 25 psig operation, LRT is the 75 psig operation and LMO is the 200 psig operation. FIG. II demonstrates that the lower ΔH (heat gain) operation to produce an olefinic gasoline permits heating the feed so that a substantial portion thereof is in the vapor phase for operating pressures up to about 900° F provided the reactor effluent temperature may go to 900° F. On the other hand, when restricting the adiabatic reactor effluent temperature to not more than 800° F, the operating pressure must be below 75 psig when processing a preheated feed comprising vapor.

Having thus generally described the invention and discussed specific embodiments in support thereof, it is to be understood that no undue restrictions are to be imposed by reasons thereof except as defined by the following claims.

We claim:

1. In a process for the catalytic conversion of methanol to form a gaoline boiling range hydrocarbons under exothermic reaction conditions within the range of 689 to 747 BTU/LB in the presence of a crystalline zeolite conversion catalyst, the improvement which comprises,
  limiting the adiabatic reactor effluent temperature of the exothermic conversion of methanol to gasoline below about 900° F by preheating the methanol feed only sufficient to take advantage of the exothermic reaction heat for providing latent heat of vaporization of the preheated feed plus the sensible heat required to take the preheated feed up to reaction temperature.

2. A method for effecting the exothermic catalytic conversion of methanol to gasoline boiling hydrocarbons at a reaction effluent temperature restricted to within the range of 600° to 900° F which comprises
  effecting the exothermic catalytic conversion of methanol at a pressure within the range of 0 to 200 psig and
  maintaining the exothermic reaction parameters within preferred limits by restricting the preheating of the methanol charged to the conversion operation within the limits defined by FIG. I.

3. A method for effecting the exothermic catalytic conversion of methanol to gasline boiling hydrocarbons at a reaction effluent temperature restricted to within the range of 600° to 900° F which comprises
  effecting the exothermic catalytic conversion of methanol at a pressure within the range of 0 to 200 psig and
  maintaining the exothermic reaction parameters within preferred limits by restricting the prehating of the methanol charged to the conversion operation within the limits defined by FIG. II.

4. The process of claim 1 wherein partially heated methanol feed is introduced sequentially to said catalyst in the direction of reactant flow.

5. The process of claim 1 wherein the crystalline zeolite conversion catalyst is selected from a class of crystalline zeolites represented by ZSM5, ZSM11, ZSM12, and ZSM21 crystalline zeolites.

6. The process of claim 1 wherein the crystalline zeolite catalyst is arranged in more than one sequential catalyst beds.

7. The process of claim 1 wherein the operation is maintained under conditions producing an aromatic gasoline product.

8. The process of claim 1 wherein the operation is maintained under conditions producing an olefinic gasoline product.

9. The process of claim 1 wherein the operating pressure is maintained below 75 psig and the methanol feed is partially vaporized.

10. The process of claim 1 wherein the operating pressure is maintained above 75 psig and the methanol feed is in a preheated liquid phase condition.

* * * * *

UNITED STATES PATENT AND TRADEMARK OFFICE
CERTIFICATE OF CORRECTION

PATENT NO. : 4,044,061
DATED : August 23, 1977
INVENTOR(S) : CLARENCE D. CHANG, ANTHONY J. SILVESTRI and JOHN C. ZAHNER It is certified that error appears in the above-identified patent and that said Letters Patent are hereby corrected as shown below:

| | |
|---|---|
| Column 1, line 29 | "conductive" should be -- conducive --. |
| Column 2, line 62 | "jand" should be -- and --. |
| Column 4, lines 13 & 14 | "centrimeter" should be -- centimeter --. |
| Column 4, line 18 | "rate" should be -- ratio --. |
| Column 4, line 68 | After "from", delete -- b --. |
| Column 5, line 22 | After "and", add -- are --. |
| Column 6, line 48 | "higher" should be -- high --. |
| Column 7, line 13 | "catalyst" should be -- catalytic --. |
| Column 7, line 63 | "seris" should be -- series --. |
| Column 7, line 68 | "feet" should be -- feed --. |
| Column 9, line 4 | "ore" should be -- more --. |

UNITED STATES PATENT AND TRADEMARK OFFICE
CERTIFICATE OF CORRECTION

PATENT NO. : 4,044,061

DATED : August 23, 1977

INVENTOR(S) : CLARENCE D. CHANG, ANTHONY J. SILVESTRI and JOHN C. ZAHNER

It is certified that error appears in the above-identified patent and that said Letters Patent are hereby corrected as shown below:

| | |
|---|---|
| Column 9, line 39 | After LQS, "in" should be -- is --. |
| Column 9, line 58 | After "form", eliminate -- a --. |
| Column 9, line 57 | "gaoline" should be -- gasoline --. |

Signed and Sealed this

Sixth Day of December 1977

[SEAL]

Attest:

RUTH C. MASON
*Attesting Officer*

LUTRELLE F. PARKER
*Acting Commissioner of Patents and Trademarks*